United States Patent
Liu

(10) Patent No.: US 9,226,525 B2
(45) Date of Patent: *Jan. 5, 2016

(54) ELECTRONIC CIGARETTE AND ELECTRONIC CIGARETTE DEVICE

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD., SHENZHEN BRANCH, Shenzhen, Guangdong Province (CN)

( * ) Notice: Subject to any disclaimer, the term of this patent is extended or adjusted under 35 U.S.C. 154(b) by 343 days.

This patent is subject to a terminal disclaimer.

(21) Appl. No.: 13/822,638

(22) PCT Filed: Nov. 22, 2012

(86) PCT No.: PCT/CN2012/085073
§ 371 (c)(1),
(2) Date: Mar. 13, 2013

(87) PCT Pub. No.: WO2014/079024
PCT Pub. Date: May 30, 2014

(65) Prior Publication Data
US 2015/0136156 A1    May 21, 2015

(51) Int. Cl.
*A24F 47/00* (2006.01)
*A61M 15/06* (2006.01)
*H05B 1/02* (2006.01)
*H05B 3/46* (2006.01)

(52) U.S. Cl.
CPC ............ *A24F 47/008* (2013.01); *A24F 47/002* (2013.01); *A61M 15/06* (2013.01); *H05B 1/0202* (2013.01); *H05B 1/0244* (2013.01); *H05B 1/0297* (2013.01); *H05B 3/46* (2013.01)

(58) Field of Classification Search
CPC ..... A24F 47/002; A24F 47/008; A61M 15/06
See application file for complete search history.

(56) References Cited

U.S. PATENT DOCUMENTS

| | | | |
|---|---|---|---|
| 2010/0307518 A1* | 12/2010 | Wang | 131/329 |
| 2011/0155153 A1* | 6/2011 | Thorens et al. | 131/329 |
| 2013/0160765 A1* | 6/2013 | Liu | 128/202.21 |
| 2014/0130816 A1* | 5/2014 | Liu | 131/329 |
| 2014/0305449 A1* | 10/2014 | Plojoux et al. | 131/328 |
| 2015/0007835 A1* | 1/2015 | Liu | 131/329 |

FOREIGN PATENT DOCUMENTS

CN           202233005     *  5/2012

* cited by examiner

*Primary Examiner* — Anthony Calandra
(74) *Attorney, Agent, or Firm* — Cheng-Ju Chiang

(57) ABSTRACT

The present invention provides an electronic cigarette and an electronic cigarette device. The electronic cigarette comprises a power supply, a liquid storage member storing liquid smoke, an atomizing unit connected to the power supply for atomizing the liquid smoke, and a controller connected with the power supply and the atomizing unit for controlling the atomizing unit to start or stop heating. The atomizing unit comprises an oil accumulating member for absorbing the liquid smoke and an electric heating piece attached to the oil accumulating member, the electric heating piece defines plural through holes. The electronic cigarette of the invention is configured with an electric heating piece in the atomizing unit instead of traditional heating wire, so that no broken fiberglass particles would be produced, to avoid the broken fiberglass particles to enter and cause harm to the human body.

15 Claims, 6 Drawing Sheets

ELECTRONIC CIGARETTE AND ELECTRONIC CIGARETTE DEVICE

CROSS REFERENCE TO RELATED APPLICATIONS

The present application is a 35 U.S.C. §371 National Phase conversion of International (PCT) Patent Application No. PCT/CN2012/085073, filed on Nov. 22, 2012, the disclosure of which is incorporated by reference herein. The PCT International Patent Application was filed in Chinese.

TECHNICAL FIELD

This invention relates to an electronic cigarette and an electronic cigarette device.

DESCRIPTION OF BACKGROUND

Please refer to FIG. 1, the electro-thermal atomization assemblies of current electronic cigarettes are all in the form of the heating wire wound fiberglass 2 to guide oil and atomize, however the fiberglass 2 after heated by the heating wire 1 is easy to produce broken fiberglass particles which can be inhaled by the users, and the broken fiberglass particles would cause harm to the human body after been inhaled.

SUMMARY

An object of the present invention is to provide an electronic cigarette, which has no broken fiberglass particles to be produced, and can avoid the harm to human body by the inhaled broken fiberglass particles.

To achieve the above object, an embodiment of the present invention provides an electronic cigarette, comprising a power supply, a liquid storage member storing liquid smoke, an atomizing unit connected to the power supply for atomizing the liquid smoke, and a controller connected with the power supply and the atomizing unit for controlling the atomizing unit to start or stop heating, the atomizing unit comprises an oil accumulating member for absorbing the liquid smoke and an electric heating piece attached to the oil accumulating member, the electric heating piece defines plural through holes.

Furthermore, the electric heating piece is bent at its opposite ends toward a same direction to form welding portions, and the welding portions defines wire welding holes therein.

Furthermore, the electric heating piece is made of nickel-chromium alloy or iron chromium aluminum alloy.

Furthermore, the oil accumulating member is made of pure cotton, chemical fiber, chemical fiber and cotton fiber hybrid material, lipophilic porous ceramic material, lipophilic porous plastic material or lipophilic porous metal material.

Furthermore, the plural through holes are uniformly arranged and has a same shape of the oval, round or polygon.

Furthermore, the electric heating piece has a rectangular, oval, circular or semicircular profile.

Furthermore, the electronic cigarette further comprises a support for insertably fixing the electric heating piece.

Furthermore, the liquid storage member has an open end, and a liquid guiding member is disposed at an outer side of the open end and connected with the oil accumulating member for guiding the liquid smoke to the oil accumulating member.

Furthermore, the controller comprises: a switch unit generating a triggering signal in responses to an external operation; and an integrated circuit electrically connected to the switch unit, and conducting the power supply and the electric heating piece according to the triggering signal.

Furthermore, the switch unit is a micro-mechanical switch or an airflow sensor.

Furthermore, the liquid storage member and the atomizing unit are provided in the sucking rod, and the sucking rod is configured with a first connector at its one end.

Furthermore, the power supply is configured in the power rod, and the power rod is configured with a second connector at its one end fittingly connected with the first connector, and an end cap at its another end.

Furthermore, the first connector and the second connector both are constructed by sequentially nested outer electrode ring, insulating ring and inner electrode ring.

The embodiment of the present invention further provides an electronic cigarette device, the electronic cigarette device comprises: an electronic cigarette as above-described; and an electronic cigarette casing for accommodating and charging the electronic cigarette.

The beneficial effects of the present invention are that: the electronic cigarette is configured with an electric heating piece in the atomizing unit instead of traditional heating wire, so that no broken fiberglass particles would be produced, to avoid the broken fiberglass particles to enter and cause harm to the human body.

The embodiments of the present invention are further described in detail as follows in conjunction with the accompanying drawings.

DETAILED DESCRIPTION OF THE EMBODIMENTS

It should be noted that, the embodiments and the characteristics in the embodiments can be mutually combined in case of no confliction; the present invention will be described in further detail below through the embodiments in conjunction with the accompanying drawings.

Figure 1:
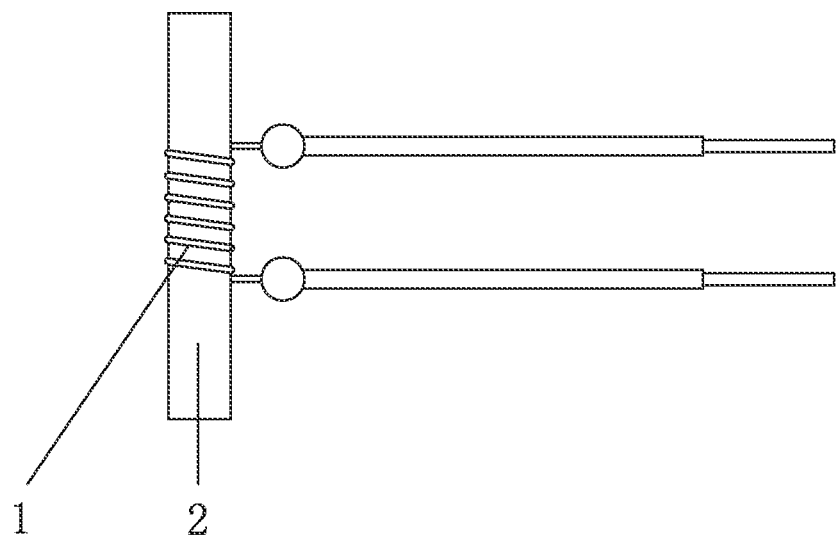
FIG. 1 is a schematic view of the electro-thermal atomization component of an existing electronic cigarette.
Figure 2:
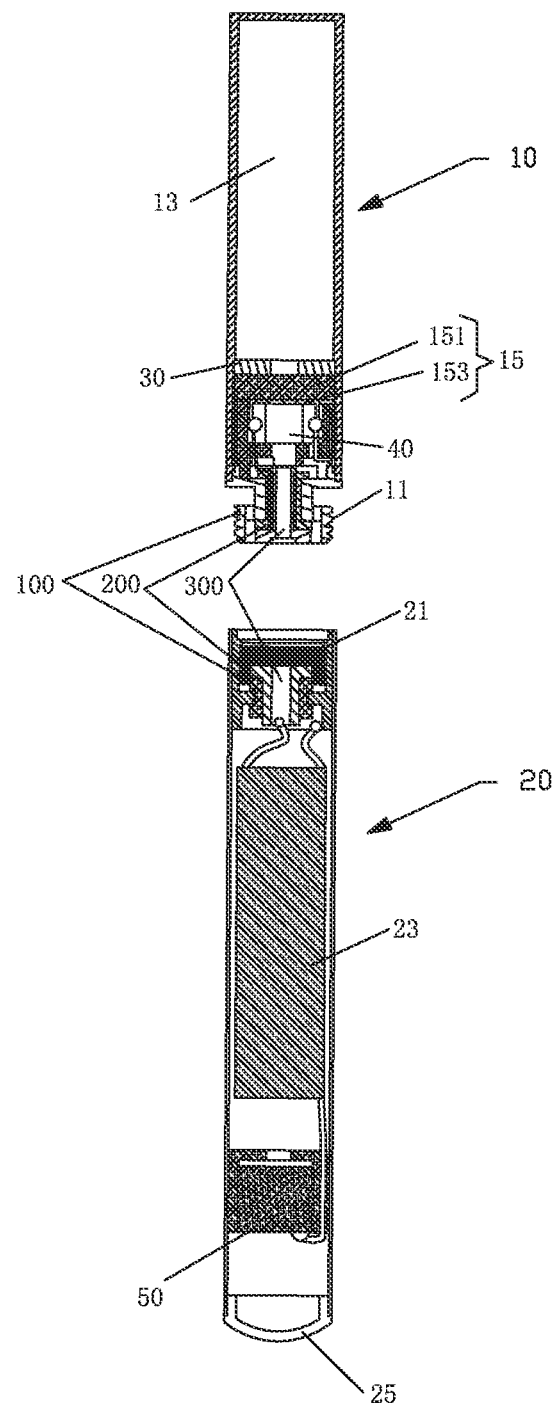
FIG. 2 is a cross-sectional view of an electronic cigarette in accordance with an embodiment of the present invention.
Figure 3:
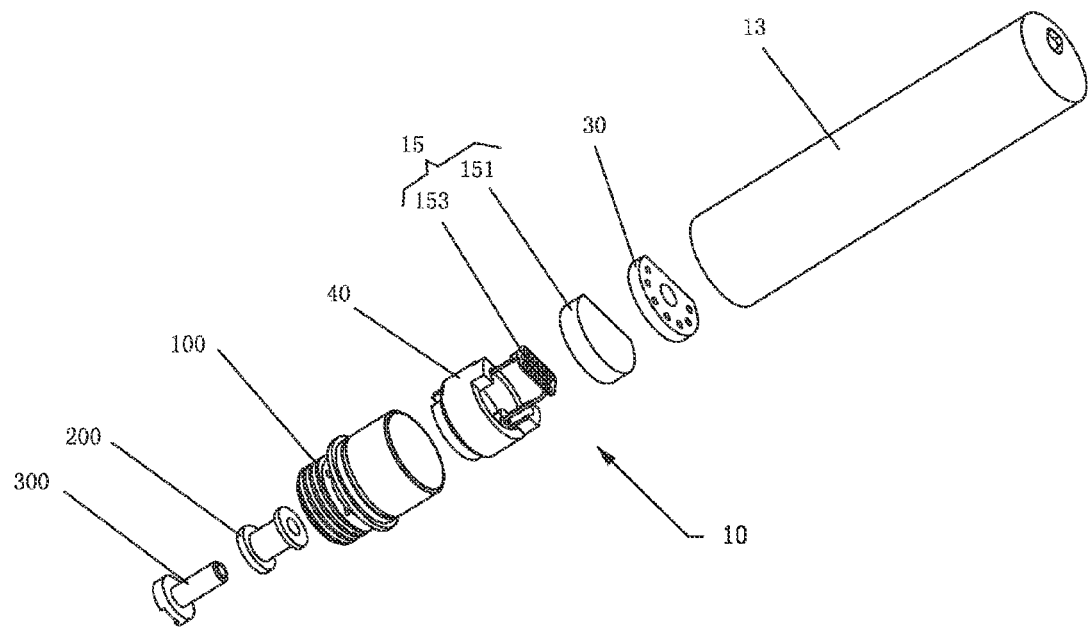
FIG. 3 is an exploded view of a sucking rod of the electronic cigarette in accordance with the embodiment of the present invention.

As shown in FIG. 2 and FIG. 3, an embodiment of the present invention provides an electronic cigarette and an electronic cigarette device, the electronic cigarette device comprises the electronic cigarette and an electronic cigarette casing for accommodating and charging the electronic cigarette.

The electronic cigarette comprises mutually fittingly connected sucking rod 10 and power rod 20. The sucking rod 10 is configured with a first connector 11 at its one end, the power rod 20 is configured with a second connector 21 at its one end fittingly connected with the first connector 11, through the first connector 11 and the second connector 21 the sucking rod 10 and the power rod 20 are connected with each other in the manner of threaded connection, snapping connection or by other means. Wherein, the first connector 11 and the second connector 21 both are constructed by sequentially nested outer electrode ring 100, insulating ring 200 and inner electrode ring 300, so as to achieve an electrical connection of the first connector 11 and the second connector 21.

The power rod 20 is configured with a power supply 23 therein, and an end cap 25 at its end away from the second connector 21.

Figure 4:
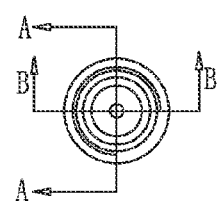
FIG. 4 is an end elevation view of the sucking rod of the electronic cigarette in accordance with the embodiment of the present invention.
Figure 5:
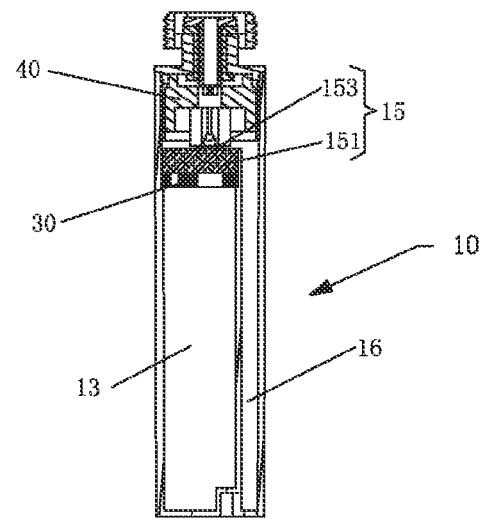
FIG. 5 is a cross-sectional view of the sucking rod as shown in FIG. 4, taken along line A-A.
Figure 6:
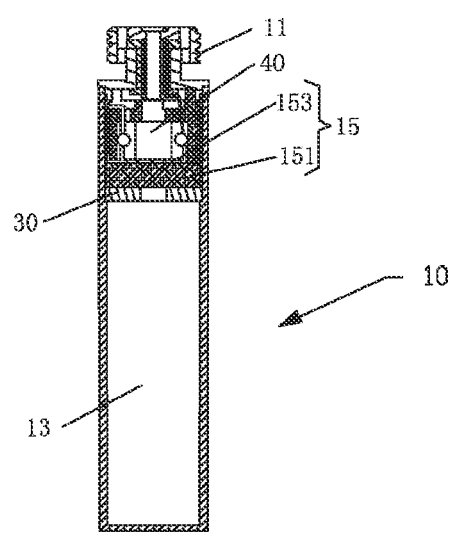
FIG. 6 is a cross-sectional view of the sucking rod as shown in FIG. 4, taken along line B-B.
Figure 7:
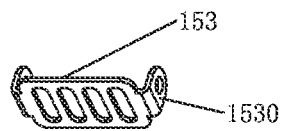
FIG. 7 is a front view of an electric heating piece in accordance with a first embodiment of the present invention.
Figure 8:
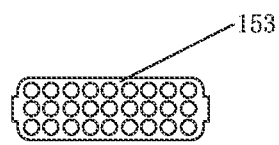
FIG. 8 is a side wall of an electric heating piece in accordance with a second embodiment of the present invention.
Figure 9:
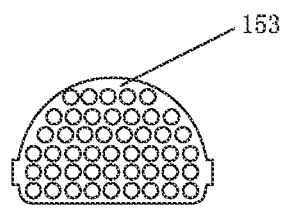
FIG. 9 is a side wall of an electric heating piece in accordance with a third embodiment of the present invention.
Figure 10:
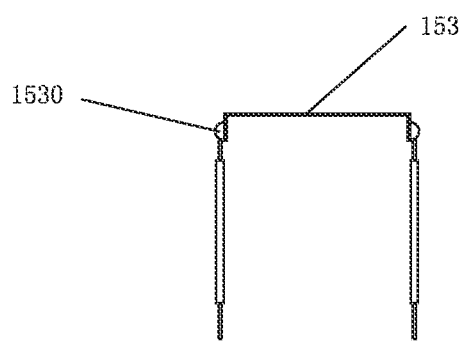
FIG. 10 is an assembled view of the electric heating piece as shown in FIG. 7.

Please refer to FIG. 4 to FIG. 6 together, in the sucking rod 10 a liquid storage member 13 for storing liquid smoke, and an atomizing unit 15 connected to the power supply 23 for atomizing the liquid smoke are provided. The liquid storage member 13 is a liquid smoke cup in the embodiment, the liquid smoke cup is used to store the injected liquid smoke for subsequent atomization by the atomizing unit 15, and is capable of being made of a material having a liquid-absorbent and fluid barrier properties, such as cotton material. The liquid smoke cup has a tube structure, and a tubular gap 16 is defined between an outer wall of the liquid smoke cup and an inner wall of a chamber of the sucking rod 10, the tubular gap 16 provides a channel for the fogged smoke to an external of the sucking rod 10 when the liquid smoke is atomized by the atomizing unit 15.

Please refer to FIG. 7 to FIG. 10 together, the atomizing unit 15 comprises an oil accumulating member 151 for absorbing the liquid smoke and an electric heating piece 153 attached to the oil accumulating member 151. The oil accumulating member 151 is made of pure cotton, chemical fiber, chemical fiber and cotton fiber hybrid material, lipophilic porous ceramic material, lipophilic porous plastic material or lipophilic porous metal material, and has good oil accumulation effect. The electric heating piece 153 is bent at its opposite ends toward a same direction to form welding portions 1530, and the welding portions 1530 defines wire welding holes therein. Since the electric heating piece 153 cannot be effectively adhered to tin, the welding portions 1530 and the wire welding holes can be used to allow the wire to pass through the wire welding holes and being twisted into a knot before welded in order to maintain a good contact of the wire with the electric heating piece 153, this can avoid the problems of cold solder joint, loose connection, bad contact etc. which are caused by direct welding the wire to the electric heating piece 153. Planes occupied by the wire welding holes can be parallel to a plane occupied by the electric heating piece 153, or perpendicular to the plane occupied by the electric heating piece 153 (see FIG. 10). The electric heating piece 153 defines plural through holes therein, and the plural through holes are uniformly arranged and has a same shape of the oval, round or polygon, on the one hand the electric heating piece 153 with a mesh structure formed by uniformly arranged plural through holes has good atomizing effect, and on the other hand has uniform distribution of heat on the electric heating piece 153. The electric heating piece 153 has a rectangular, oval, circular or semicircular profile, and is matched with the oil accumulating member 151 in shape and size. The electric heating piece 153 is made of nickel-chromium alloy or iron chromium aluminum alloy, so that it is good in thermal performance, and rapid in heating.

The electronic cigarette further comprises a liquid guiding member 30, and a support 40 for insertably fixing the electric heating piece 153. Specifically, the liquid smoke cup has an open end, and the liquid guiding member 30 is disposed at an outer side of the open end and connected with the oil accumulating member 151 for guiding the liquid smoke to the oil accumulating member 151, the liquid guiding member 30 and the support 40 both are arranged within the sucking rod 10, in the embodiment the liquid guiding member 30 is an oil baffle, and the oil baffle has its one side abutting against the open end of the liquid smoke cup, and its another side abutting against the oil accumulating member 151, the oil baffle defines through holes therein for the liquid smoke to pass through; the support 40 is made of silica gel or other heat-resistant insulating materials.

The electronic cigarette further comprises a controller (not shown) connected with the power supply 23 and the atomizing unit 15, for controlling the atomizing unit 15 to start or stop heating. The controller comprises a switch unit and an integrated circuit.

The switch unit generates a triggering signal in responses to an external operation. The switch unit is a micro-mechanical switch configured on a sidewall of the electronic cigarette or an airflow sensor 50 located in the power rod 20, in the embodiment the switch unit exemplarily illustrated is an airflow sensor 50.

The integrated circuit is electrically connected to the switch unit, and can conduct the power supply 23 and the electric heating piece 153 according to the triggering signal. The integrated circuit is configured on a circuit board, and the circuit board is located in an inner chamber of the electronic cigarette.

Though the embodiments of the present invention have been illustrated and described, for the persons of ordinary skill in this field, various changes, modifications, replacement and variations within the principle and spirit of the present invention can be made to the embodiments, the protecting scope of the present invention is defined by the appended claims and their equivalents.

What is claimed is:

1. An electronic cigarette comprising a suckinging rod and a power rod with a power supply therein; the sucking rod therein comprising a liquid storage member storing liquid smoke, and an atomizing unit connected to the power supply for atomizing the liquid smoke, wherein the atomizing unit comprises an oil accumulating member for absorbing the liquid smoke and an electric heating piece attached to the oil accumulating member, the electric heating piece defines plural through holes;

the electric heating piece has a mesh structure and is matched with the oil accumulating member in shape and size;

the liquid storage member is a liquid smoke cup, and has a tube structure;

the electronic cigarette further comprises a liquid guiding member, and a support for insertably fixing the electric heating piece; the liquid smoke cup has an open end, and the liquid guiding member is disposed at an outer side of the open end and connected with the oil accumulating member for guiding the liquid smoke to the oil accumulating member; the liquid guiding member and the support both are arranged within the sucking rod;

the liquid guiding member is an oil baffle, and the oil baffle has a first side thereof abutting against the open end of the liquid smoke cup, and a second side opposite the first side abutting against the oil accumulating member; and a first side of the oil accumulating member abuts against the second side of the liquid guiding member, a second side of the oil accumulating member opposite the first side thereof abuts against the electric heating piece; and the oil baffle defines through holes therein for the liquid smoke to pass through.

2. The electronic cigarette as described in claim 1, wherein the electric heating piece is bent at its opposite ends toward a same direction to form welding portions, and the welding portions defines wire welding holes therein; wire passes through the wire welding holes and being twisted into a knot, and then is welded to the electric heating piece whereby to maintain a good electrically contact of the wire with the electric heating piece; and planes occupied by the wire welding by the electric heating piece, or perpendicular to the plane occupied by the electric heating piece.

3. The electronic cigarette as described in claim 1, wherein the electric heating piece is made of nickel-chromium alloy or iron chromium aluminum alloy.

4. The electronic cigarette as described in claim 1, wherein the oil accumulating member is made of pure cotton, chemical fiber, chemical fiber and cotton fiber hybrid material, lipophilic porous ceramic material, lipophilic porous plastic material or lipophilic porous metal material.

5. The electronic cigarette as described in claim 1, wherein the plural through holes are uniformly arranged and has a same shape of the oval, round or polygon.

6. The electronic cigarette as described in claim 1, wherein the electric heating piece has a rectangular, oval, circular or semicircular profile.

7. The electronic cigarette as described in claim 1, wherein a controller is connected with the power supply and the atomizing unit for controlling the atomizing unit to start or stop heating; the controller comprises: a switch unit generating a triggering signal in responses to an external operation; and an integrated circuit electrically connected to the switch unit, and conducting the power supply and the electric heating piece according to the triggering signal.

8. The electronic cigarette as described in claim 7, wherein the switch unit is a micro-mechanical switch or an airflow sensor.

9. The electronic cigarette as described in claim 1, wherein the liquid storage member and the atomizing unit are provided in the sucking rod, and the sucking rod is configured with a first connector at its one end.

10. The electronic cigarette as described in claim 9, wherein the power supply is configured in the power rod, and the power rod is configured with a second connector at its one end fittingly connected with the first connector, and an end cap at its another end.

11. The electronic cigarette as described in claim 10, wherein the first connector and the second connector both are constructed by sequentially nested outer electrode ring, insulating ring and inner electrode ring.

12. The electronic cigarette as described in claim 1, wherein the liquid smoke cup is used to store the injected liquid smoke for subsequent atomization by the atomizing unit, and is capable of being made of a material having a liquid-absorbent and fluid barrier properties.

13. The electronic cigarette as described in claim 1, wherein the liquid smoke cup is capable of being made of cotton material.

14. The electronic cigarette as described in claim 1, wherein the support is made of silica gel or other heat-resistant insulating materials.

15. The electronic cigarette as described in claim 1, wherein a tubular gap is defined between an outer wall of the liquid smoke cup and an inner wall of a chamber of the sucking rod, the tubular gap provides a channel for fogged smoke to an external of the sucking rod when the liquid smoke is atomized by the atomizing unit.

* * * * *